United States Patent [19]

Crane et al.

[11] 4,078,656

[45] Mar. 14, 1978

[54] KIT FOR OBTAINING SPECIMEN ON A GLASS SLIDE

[75] Inventors: Walton B. Crane, Sherman Oaks; Frederic L. Nason, Los Angeles, both of Calif.

[73] Assignee: Medical Packaging Corporation, Santa Monica, Calif.

[21] Appl. No.: 713,864

[22] Filed: Aug. 12, 1976

Related U.S. Application Data

[63] Continuation-in-part of Ser. No. 622,478, Oct. 15, 1975, abandoned, which is a continuation-in-part of Ser. No. 546,495, Feb. 3, 1975, abandoned, which is a continuation-in-part of Ser. No. 450,313, Mar. 12, 1974, abandoned.

[51] Int. Cl.² .................... A61J 1/00; B65D 75/14; B65D 75/38
[52] U.S. Cl. .................. 206/223; 128/2 W; 206/362.4; 206/370; 206/456; 206/474; 206/491
[58] Field of Search .............. 229/92.1, 92.3, 92.7, 229/73, 51 DB, 87 R; 128/2 W; 206/45.14, 223, 361, 362.4, 363, 370, 438, 456, 474, 491, 229

[56] References Cited

U.S. PATENT DOCUMENTS

| 730,933 | 6/1903 | Lawson | 229/92.7 |
|---|---|---|---|
| 1,167,245 | 1/1916 | Abrams | 229/92.7 |
| 1,615,200 | 1/1927 | Shrum | 229/40 |
| 2,320,018 | 5/1943 | Ullman | 229/40 |
| 2,985,288 | 5/1961 | Reich | 206/363 |
| 3,143,273 | 8/1964 | Bunting et al. | 229/40 |
| 3,525,469 | 8/1970 | Sawoon | 229/92.7 |
| 3,711,012 | 1/1973 | Cytron et al. | 229/73 |

*Primary Examiner*—William Price
*Assistant Examiner*—Joseph Man-Fu Moy
*Attorney, Agent, or Firm*—Forrest J. Lilly

[57] ABSTRACT

A package is provided for containing and delivering to a physician, laboratory or hospital a glass slide fastened removably in position, spatula, tongue depressors, etc., for use in obtaining a specimen, and retaining it on the glass slide during transportation to the laboratory for analysis. The package comprises two side panels, joined by a narrow end wall, with end walls also at the remote ends of the panels, also edge walls, and side flaps. After the specimen has been deposited on the glass slide, the side flaps are severed, so they can be folded over independently of one another. The package can then be folded into a smaller one, more compact by about one-half the original length, for transportation or mailing to the laboratory. Features are provided for protection of the deposit on the glass slide from the opposed wall portions of the package.

In a modified form of the invention, the package is somewhat as described above, excepting that provisions are made for tearing away one of the side panels and two of the side flaps just prior to the final folding and mailing to the laboratory. The folded package then does not have so many thicknesses of paper stock, but sufficient when a plastic slide is used, or a bracing frame is used for the glass slide.

13 Claims, 20 Drawing Figures

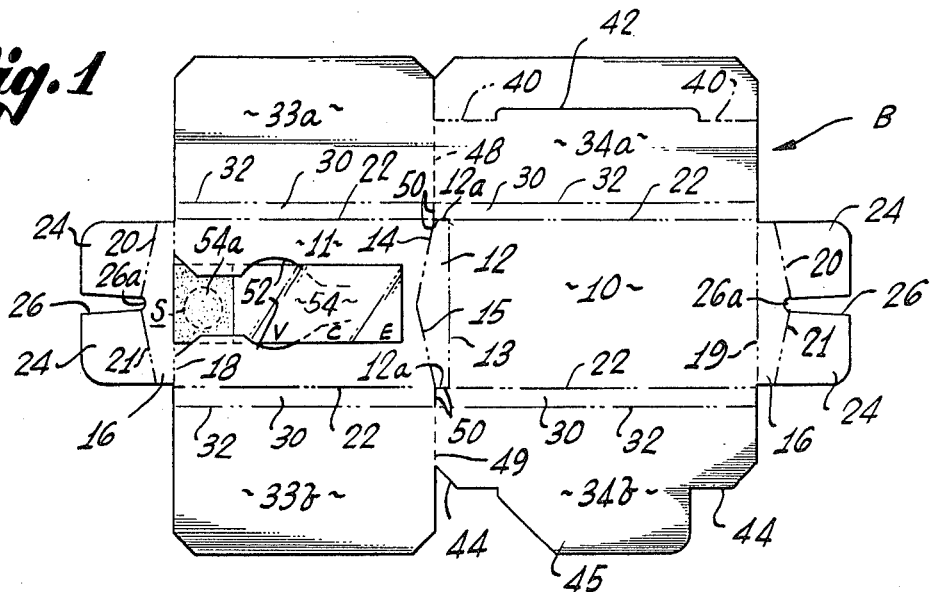
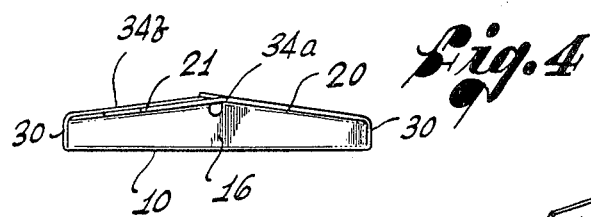
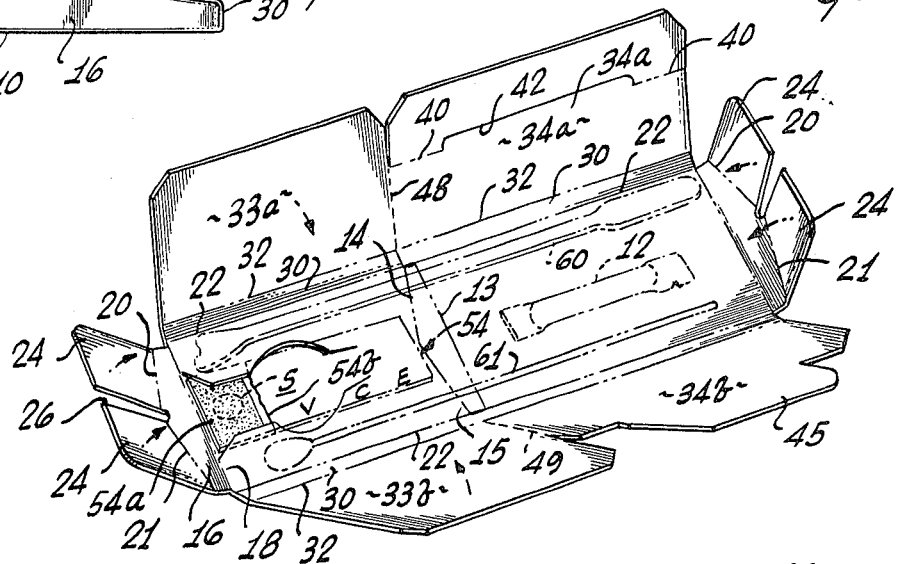
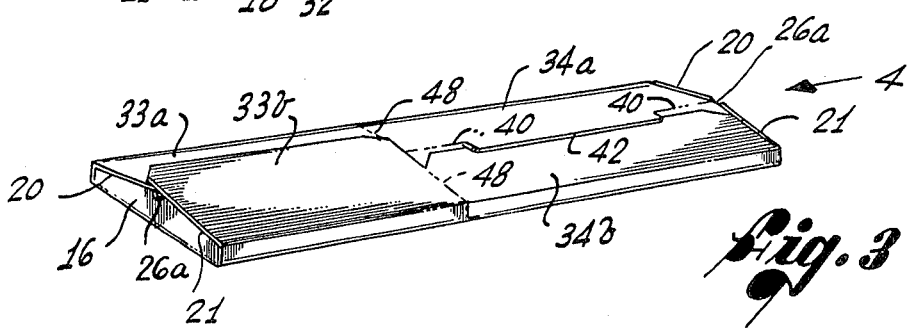

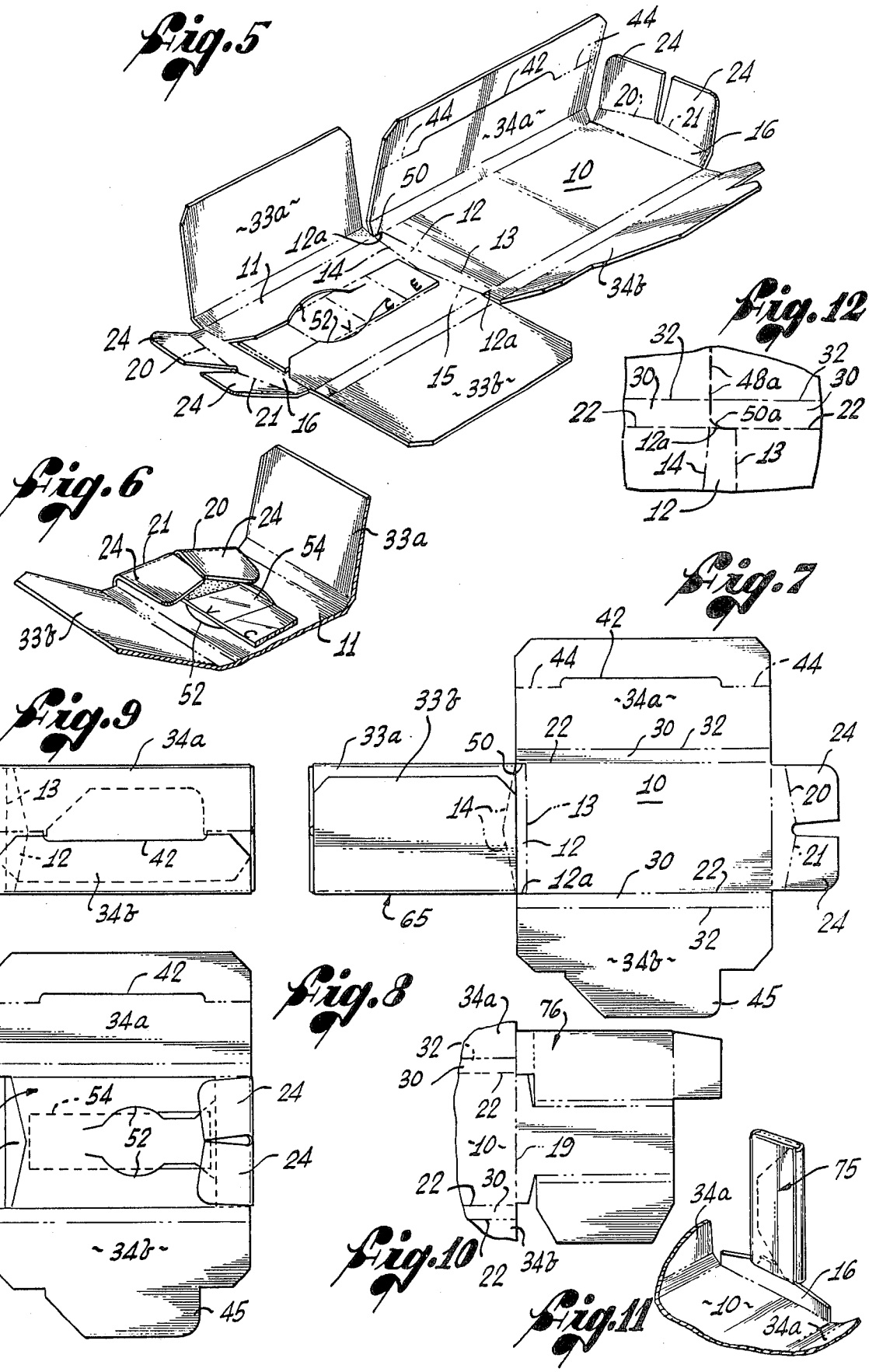

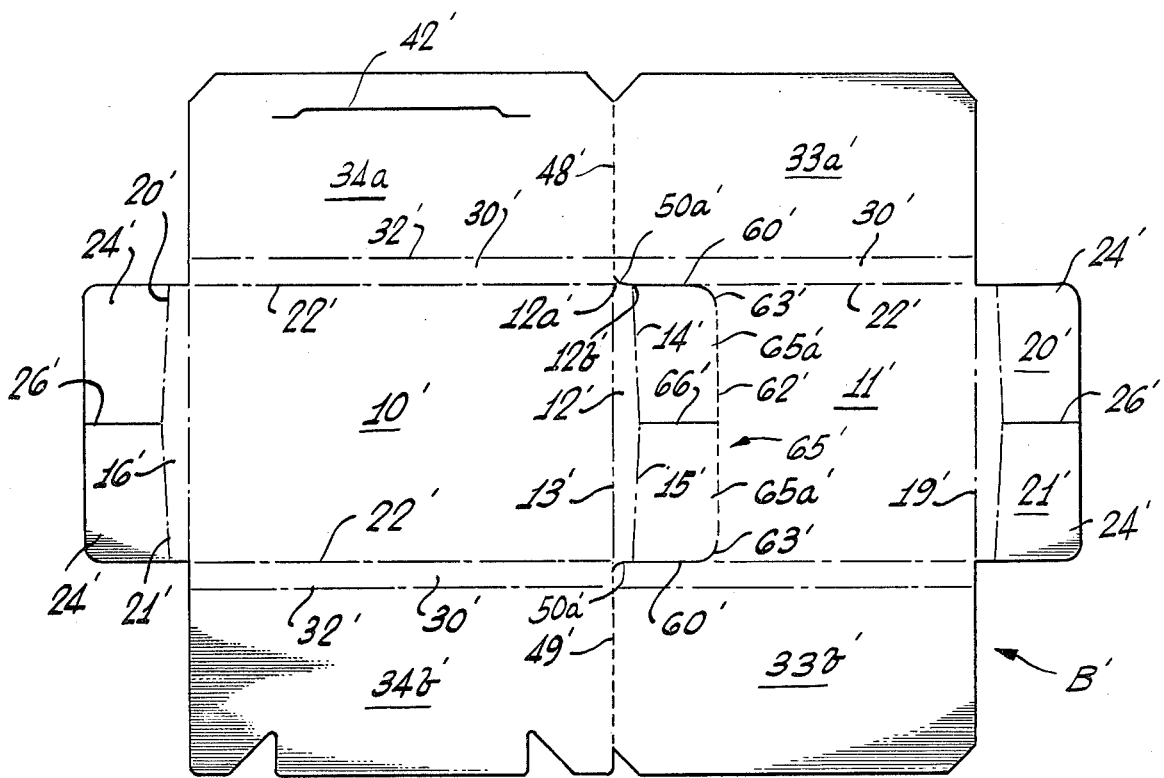
Fig. 13
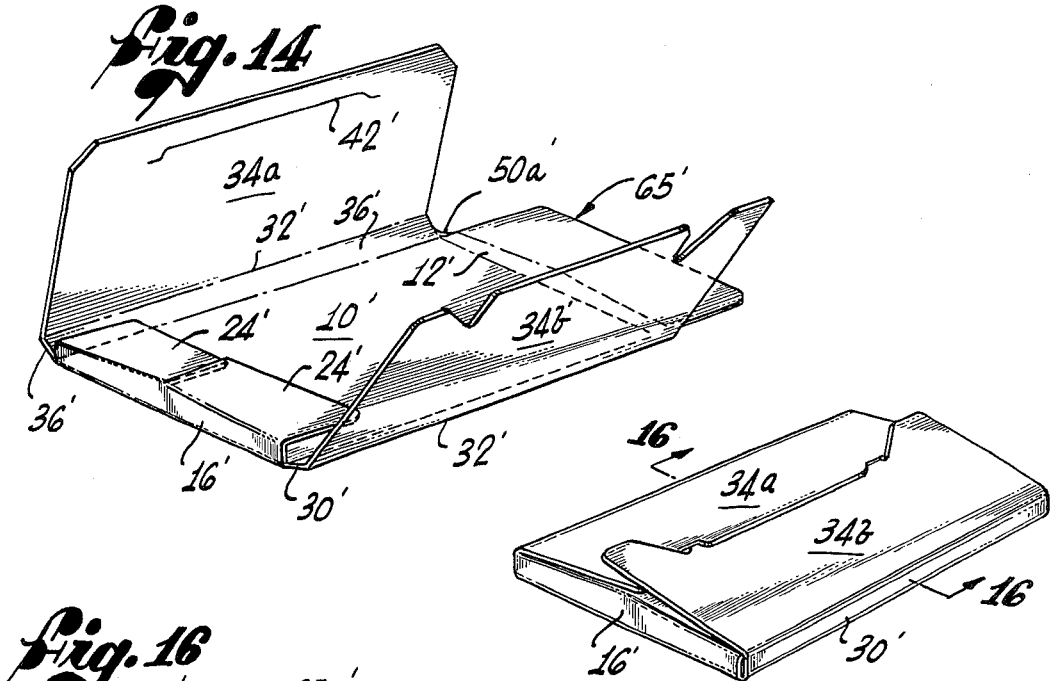
Fig. 14
Fig. 15
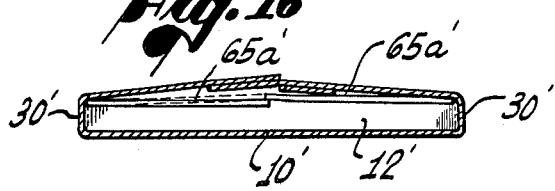
Fig. 16

KIT FOR OBTAINING SPECIMEN ON A GLASS SLIDE

RELATED APPLICATION

This application is a continuation-in-part of our earlier application Ser. No. 622,478, filed Oct. 15, 1975, and allowed May 17, 1976, now abandoned, which was a continuation-in-part of our application Ser. No. 546,495, filed Feb. 3, 1975, now abandoned, which was in turn a continuation-in-part of our original parent application Ser. No. 450,313, filed Mar. 12, 1974, for PACKAGE, and allowed July 23, 1975 and now abandoned.

FIELD OF THE INVENTION

This invention relates generally to packages, and more particularly to packaging of scrapings of possibly bacteria-carrying material, or cellular material, for transportation to the laboratory for identification.

BACKGROUND AND BRIEF SUMMARY OF THE INVENTION

The so-called Pap test for identification of malignant or pre-malignant cellular matter found in surgical scrapings from the cervix is now widely established. A general purpose of this invention is the provision of a package containing, initially, a glass slide, and implements such as a spatula, swab, tongue depressor, and/or other supplies, that may be needed by a physician in obtaining and receiving the scrapings, and that, upon opening, serves as a surgical tray to hold such implements and the glass slide. The package, in its initial form, is made long enough to contain all such implements. The package has additional features, however, by which, after the implements have been used to obtain the scrapings and deposit them on the glass slide in the package, and have been discarded, it may, by making certain tears along certain predetermined and pre-weakened tear lines, be reconstructed and refolded into a new compact form of package of reduced size but doubled wall thickness, and therefore of increased strength for transportation to the laboratory, for example, in the mails.

In a modified form, for situations not requiring such increased strength, e.g., when a plastic rather than glass slide is used, a portion of the original long package is torn away, along a predetermined line of weakness, and the remainder of the package then closes with reduced dimensions.

BRIEF DESCRIPTION OF THE DRAWINGS

FIG. 1 is a view of a blank form from which the package of the invention is erected;

FIG. 2 is a perspective view of the package in open condition and showing, in phantom lines, articles such as to be packed therein, the glass slide being shown in full lines;

FIG. 3 is a perspective view of the package of FIG. 2 folded into a closed position;

FIG. 4 is an end elevational view of the package;

FIG. 5 is a perspective view of the package, after re-opening, and after tearing certain lines of perforations;

FIG. 6 is a perspective view showing a pair of end flaps in an angular plane folded down to cover but give clearance over an ear on a glass slide;

FIG. 7 is a plan view of the package at an intermediate stage of re-folding thereof;

FIG. 8 is a plan view of the package in a succeeding position of re-closing;

FIG. 9 is a plan view of the completely closed package, with the closure side flaps overlapped and interlocked;

FIG. 10 is a perspective view of a modification added to one end of the package, shown in a position prior to folding;

FIG. 11 is a perspective view showing the modification in its completed condition, in position for use;

FIG. 12 is a fragmentary view showing a preferred modification of a portion of FIG. 1;

FIG. 13 is a blank showing a modified package with predetermined lines of weakness affording fold and tear lines;

FIG. 14 shows in perspective a carton partially folded from the blank of FIG. 13, after tearing along the tear lines and discarding an excess portion of the package when reconstituted for mailing of the enclosed specimen;

FIG. 15 shows the carton after the tear-away of its discarded portion (FIG. 14) of the original carton, and final folding to closed position;

FIG. 16 is a section on line 16—16 of FIG. 15;

DESCRIPTION OF AN ILLUSTRATIVE EMBODIMENT

Figure 17:
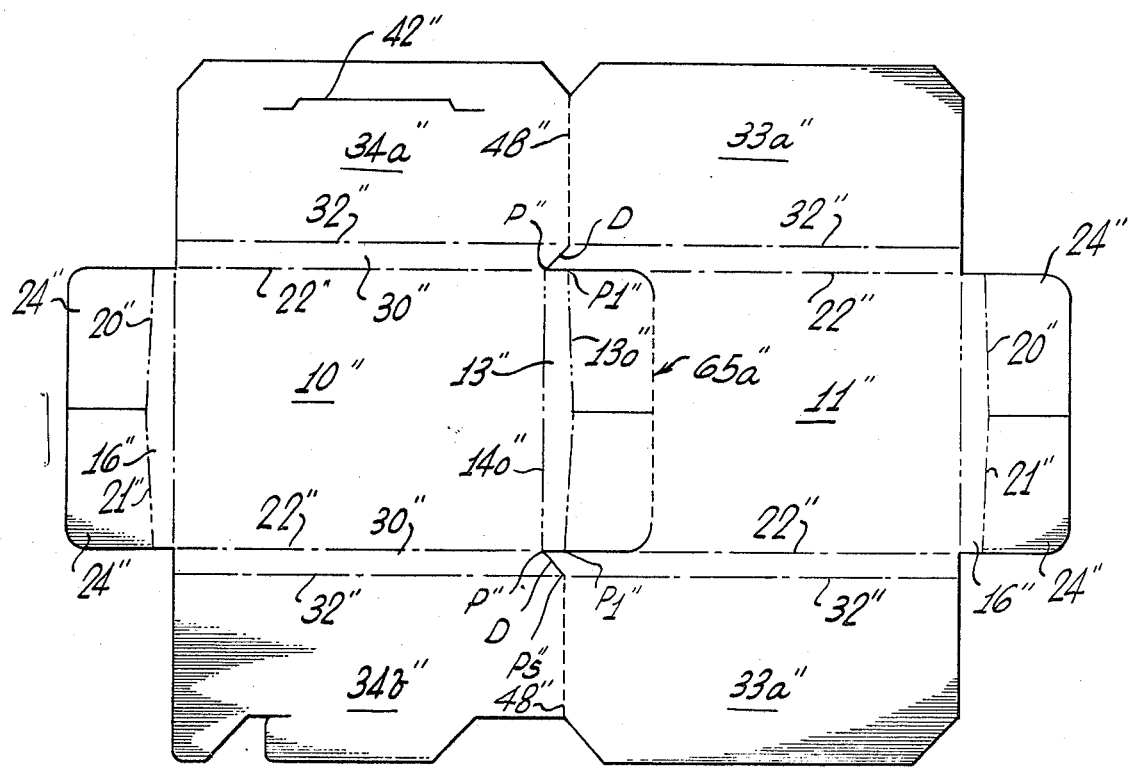
FIG. 17 is a view similar to FIG. 13, but showing an equivalent modification.

The package of the invention in its first form is erected from the paperboard blank B (FIG. 1), which is scored and perforated along certain lines for folding or tearing to carry out the purposes of the invention.

This blank embodies two longitudinal side panels 10 and 11, joined end to end by a low intermediate end wall 12 defined at its right hand edge, as viewed in FIG. 1, by a straight score line 13 at right angles to the panels 10 and 11, and at its other edge by a score line in the shape of a saddle type roof line or hip 14, 15. Similar end walls 16 are joined to the opposite ends of panels 10 and 11, along straight score lines 18 and 19, the saddle roof score lines 20, 21 of these end walls 16 facing away from the panels 10 and 11. For convenience herein and in the claims, the side panel 10 is termed herein as the bottom side panel, and the panel 11 is termed the top side panel.

The panels 10 and 11 are bordered by longitudinal score lines 22. The ends 12a of end wall 12 are included in the longitudinal score lines 22, and the ends of end walls 16 as well as the outer edges of two end flaps or tabs 24 joined to roof line portions 20 and 21 are in rectilinear alignment with score lines 22. The two tabs 24 at each end of the blank are divided by slits or cut-outs, preferably in the form of convergent end notches 26 having rounded, relatively wide bottoms 26a.

Side edge walls 30 are defined by score lines 32 parallel with the score lines 22 and outside the latter by a spacing distance equal to, or just slightly less than, the height dimension of the end walls 12 or 16 at the ends of same.

Flaps 33a and 33b hinging on the score lines 32, and of lengths substantially equal to or preferably a little shorter than, the length of the panel 10 between end walls 12 and 16, are formed along the score lines 32 of panel 11. They are adapted to largely overlap one another, as appears in the drawings.

Flap 34a, contiguous to the flap 33a, hinges on the same score line 32 across said flaps 33a and 34a; and the same is true for the flaps 33b and 34b, and their common score line 32.

Short score lines 40, parallel with score lines 32 and 22 and rectilinearly aligned with one another, extend inwardly for short distances from the end edges of the flaps 34a, and are there connected with the curved opposite ends of a slit 42. The opposite flap 34b is cut with shoulders 44 to form a locking tongue 45 adapted to be received in slit 42 to form a conventional type of closure. The junction lines between the flaps 33a and 34a are severed outwardly of score lines 40, and are perforated inwardly of score lines 40 to score line 32, as at 48. Between the flaps 33b and 34b, the corresponding junction line is perforated at 49, beginning at score line 32, and ending at shoulder 44. Extending inwardly from these perforations, across edge walls 30 to score lines 22, and thence along ends 12a of end wall 12 to bottom edge score line 13, are right-angle cuts 50. Tears are made along these perforated lines in a later described stage in the use of the package.

The panel 11 may be cut with slits 52, curved as shown, to removably hold a glass slide 54 (or plastic slide, now available) in the manner shown in FIG. 1. A glass slide may also be supported by a transparent plastic frame or brace, not shown. The conventional glass slide has a frosted end 54a, on which the patient's name may be written, and formed along the slide are three areas designated by the letters V, C and E on which different smears may be placed. Alternatively, and preferably, the glass slide is removably fastened to the panel 11, in the position shown in FIG. 2, by use of a spot s of pressure sensitive adhesive, the spot of adhesive being preferably under the left hand end portion 54a of the slide, where its appearance is obscured by the usually frosted left-hand end portion of the slide. If the adhesive spot s is used, the slits 52 may of course be omitted. Glass slides formed with letters as described above are relatively expensive, however, and in FIG. 2 (where the glass slide is broken away at 54, and represented in phantom lines therebeyond), these letters are printed on the panel 11, preferably in color, just under the positions they would otherwise occupy on the initial form of the glass slide. These letters may be printed on with a colored glue, which thus cooperates in holding the glass slide down.

To fold the box into its closed position, prior to making the perforation tears at 48 and 49, the implements typically supplied the physician with the package are placed therein, as shown in FIG. 2. These implements may include the glass slide 54, spatula 60, swab 61 and tube 62 of substance for forming a protective coating over the smears deposited on the glass slide. With these in place, the end tabs 24 are all folded over, and the pairs of side panels 33a, 34a and 33b, 34b, still undivided at 48 and 49, are overlapped over the end tabs 24 and over one another, with locking tongue 45 inserted in slit 42, so as to appear then as shown in FIG. 3.

Note will be taken (FIG. 3) that the saddle "roof-line" given the end walls elevates the longitudinal center ridge line or "hip" of the package, so that it will afford added clearance space over the generally centrally located glass slide. This prevents cellular material later deposited on the glass slide from being scraped or rubbed off.

At this time, with the package filled and closed, in condition to be shipped in quantity to the physician, hospital or laboratory, the flaps 34a and 34b may be locked to one another, as here shown, or the flap pairs may simply be overlapped and temporarily closed, as by a spot of adhesive or glue, not shown.

When the packaged implements are to be used, the package is opened to return it to the position of FIG. 2, and then serves as a tray for the implements, for the convenience of the doctor who is taking the specimen.

Finally, the smear having been taken and deposited on the glass slide, and protected by coating over with a layer of the coating substance provided, the package is reclosed but, since the relatively long spatula, swab, etc. are now discarded, in a different manner whereby the carton is both shortened and strengthened. First, the perforations at 48 and 49 are torn, so the side flaps are severed at their edges to the cuts 50 (FIG. 5). The end wall 16 and the two end tabs 24 at the glass slide end of the package are then bent inward and down. The end wall 16 bends through 90°, on the score line 19, and the tabs 24 bend through a little more than 90° on the oppositely angled score lines 20 and 21, until they move into tilted planes, their corners engaging the bottom panel 11 just outside the slits 52, so that they tilt up over the glass slide. From FIG. 6, it will be seen that the tabs 24 hinged at the angular score lines 20 are thus tilted relative to the glass slide, and have ample clearance thereover. The tabs 24 thus do not contact any surface area of the slides where specimen deposits may have been made. The hip roof line feature 20, 21 is much preferred; but is not absolutely indispensable, and could be replaced by a straight edge.

Beyond the position indicated in FIG. 6, the flaps 33a and 33b are folded over, to reach the position of FIG. 7, and the packet 65 consisting of the side panel 11 and flaps 33a and 33b overlapped over the tucked-in end tabs 24, is folded over, through 180°, to the position of FIG. 8. The end wall 12 bends on the score line 13, turning actually through more than a right angle, as indicated. The end tabs 24 at the right have also been bent in over the end of the packet 65 to reach the position of FIG. 8. The flap 34a is then folded down, and the opposite flap 34b then folded over, and its locking tongue 45 inserted in the slit 42.

The package is then fully closed (FIG. 9), and may be carried, or mailed, to the laboratory, with its contents fully protected.

The package has several novel features which should be especially mentioned. First, the package in its first use has to have a length adequate to contain the usual spatula, swab and perhaps a tongue depressor; but after these elements have been used, they are discarded. The package then may be reduced in length by substantially half its length. Moreover, this reduction in length permits more stock to be used in the side walls. Actually, the side walls of the final package are of four ply thickness on one side, and three on the other, thus becoming not only more compact, but of increased strength and protection for the enclosed glass slide and specimen. Finally, the angled roof lines 20 and 21 and longitudinal ridge line provided thereby give the package a high center, and thus protective clearance, over the glass slide.

FIGS. 10 and 11 show a modification, in which the two tabs 24 at the opposite end of the package from the glass slide are replaced by a paperboard tube 75 folded from stock 76 which replaces the tabs 24. This stock is formed into panels, flaps and tabs by score lines and cuts as clearly shown in FIG. 10, and as may be folded in an obvious manner into the holder tube 75. In this tube may be inserted implements which the physician may require, such as spatula, tongue depressor and/or swab, and which are held in a convenient position and by the sterilized holder tube 75, at an angle such as shown, above the supporting table or tray.

FIG. 12 is a fragmentary view of a portion of FIG. 1, but showing a preferred modification which has been found a useful expedient in the manufacture of the package.

The transverse tear or disconnect line 50a is formed of the intermittent end-to-end slits 48a, which cross and form a junction with the lines 32, and which are turned or re-directed within the right-hand edge wall (in FIG. 12) to reach and terminate at the junction thereof with the corresponding termination of the score line 13. In this case, the disconnect line 50a turns and joins the end edge 12a at an intermediate point. The reason for this construction is that the line 50a can be cut readily by a single curved blade, whereas the right angle cut which it replaces requires two blades at right angles. The curved cut of FIG. 12 is accordingly the preferred form of the package otherwise shown in FIGS. 1–11. Thus, with this preferred shaping, the paperboard stock bends when the container is closed in a manner generally achieved by the first described embodiment. The form of FIG. 12, however, has the advantage that two successive right angle cuts 50 are no longer required, and a single appropriately curved cutter can make the desired cut 50a in one stroke.

The preferred practice of the invention thus utilizes the single cut or slit 50, which misses by an immaterial distance the exact upper corner of the end wall.

Following the tearing of the attachment points between perforations 48a, and thus accomplishing a severance to the slit 50a the small triangle of stock between the curved extremity of the slit 50a and the end edge 12a adjacent the upper corner of the end wall, simply bends with the edge wall 30 along the score line 22, with no problem. This exact shaping, however, is still purely illustrative, and subject to further change as will be pointed out hereinafter.

Reference is next directed to FIGS. 13 to 16, showing another embodiment of the invention. By comparison of FIGS. 1 and 13, it will be seen that, among other things, the blank B' of FIG. 13 is in effect, or for the most part, reversed right for left. However, with this understanding, many parts of the modified package of FIGS. 13 et seq. correspond with parts of the package of FIGS. 1–12, and will for convenience be identified by corresponding reference numerals, but with primes annexed in the case of FIGS. 13–16, with minimized further description excepting to explain in what ways the embodiment of FIGS. 13–16 differs in construction and use from that of FIGS. 1–12.

The parts 10' and 11', excepting for end to end reversal, correspond generally to parts 10 and 11 of FIGS. 1 and 2. According to the nomenclature used, part 10' is a permanent bottom side panel, and panel 11' a tear-away side panel. The transverse lines 48' and 49' of perforations or tear slits across the flaps 33a', 34a' and 33b' and 34b' extend inwardly across the edge fold lines 32' and most of the way inwardly across edge walls 30', in rectilinear alignment with the score line marking the base edge 13' of the end wall 12'. Each slit 50a', which substantially, partially, or nearly disunites the end edge 12a' of the end wall 12' from the edge wall 30' between the base and top edges 13' and 14', 15' of the end wall 12', begins at the corresponding extremity 12b' of the top edge 14' or 15' of said end wall 12', follows substantially along the end wall edge 12a' for a part of the length of the latter, and then, turning in general proximity to the corresponding lower corner of the end wall, curves away from the edge 12a' so as to confront or oppose the inner end of the tear line of perforations or slits 48'. With this arrangement, the paperboard stock bends on score line 13', deforming to allow the bend in the region between the left hand end portion of edge 12a' and the curved extremity of the slit 50a'.

From the right hand end points 12b' of the edges 12a' of end wall 12' (as viewed in FIG. 13), a line of severance 60' is formed in or along the score line 22' and these lines of severance extend for a distance as illustrated, and then turn toward one another, as at 63' and join as a weakened, e.g., perforated, transverse line of severance 62'. The junctions of the lines of severance 60' with the transverse line of severance 62' are preferably connected by severed arcs 63. The lines 14', 15', 60', 63', 62', 63' and 60' form a flap 65', which is severed into two flaps 65a', side by side, by a cut 66'. The lines of severance 60' may be pre-cut, or may be lines of weakness permitting tearing. Perforations may be used. FIG. 13 may be taken as broadly illustrating a line of severance, and the severance step may be taken prior to first use of the package, or after the package has been used to contain the implements in preliminary warehousing or transportation to the doctor or clinic, a specimen has been deposited on the container glass or plastic slide, and the package is ready for re-closure. The cut or slit at 66' dividing the flap into two parts 65a' may be made prior to the first stage of use of the package, or may be made by tearing along a weakness line, such as a line of perforations, as the package is prepared for final mailing.

Thus, the package of FIGS. 13–16 will be understood to contain initially a glass or plastic slide, not shown, but secured in any fashion within the left hand portion of the package, e.g., much as illustrated in FIGS. 1 and 2. With the glass or plastic slide, and other implements in place, the package is folded and locked closed, in the manner of the embodiment of FIGS. 1–3. After opening of the package, and use of its contents, as with the earlier embodiment, the parts of the package to the right of the severance lines 48' and 49', and of the curved slits 50a', corner cuts 63', and weakened, e.g., perforated, severance line 62', are detached and discarded. If the flap edges defined by severance lines 60' have not been pre-severed, they will also, of course, be severed to completely free the portion of the package to be discarded.

Finally, with a specimen deposited on the glass or plastic slide (not shown in FIGS. 13–16, but understood to be contained with the remainder of the carton), for example, in the manner of FIGS. 1–12, or otherwise, the carton, with the throw-away portion removed, is folded and locked closed, in the manner shown in FIGS. 15 and 16.

Reference is next directed to a modification of the embodiment shown in FIGS. 11–16. This embodiment, shown in FIGS. 17–20, is substantially an equivalent of that of FIGS. 11–16, with most features in common. Precisely corresponding features will be identified with corresponding reference numerals but double primed in FIGS. 17 to 20, and will not all be described. Features in FIGS. 17-20 not precisely as in FIGS. 13-16 will in most cases be distinguished with double primes and sub-zeros.

In FIGS. 17-20, the side panel 10" is a permanent, bottom side panel, and panel 11" is a temporary top side panel. The interposed transverse end wall 13" may be described as having lower longitudinal edge 14$_o$", hinged to the proximate lower end edge of the permanent side panel 10", and an opposite upper longitudinal edge 13," to which is hinged the divided tear flap 65$_o$". The terminals of the lower longitudinal edge 14$_o$" of wall 13" meet score line 32" at points P", and the terminals of the upper longitudinal edge 13$_o$" intersect the terminals of upper longitudinal edge 13$_o$" at P$_1$". On score lines 32", at points Ps", positioned laterally outward of points P$_1$", are the beginning points of disconnect lines D, which may be pre-weakened by perforation, or may be pre-cut. The end points of these disconnect lines meet the aforementioned points P" at the junctions of the lower panel edges 22" with the transverse bottom hinge line 14$_o$" of the end wall 13".

Severance lines 48", pre-cut or perforated, extend transversely across the side panels 33a" and 34" to points Ps". Perforated or pre-cut lines 12a" extend oppositely from the edge score lines 22" of panel 10" across the ends of end walls 13", and thence continue along score lines 22" of the tear-away panel 11" for a distance as illustrated, and thence turn transversely across the side panel 11" to join and form the divided or split flap 65$_o$".

Figure 18:
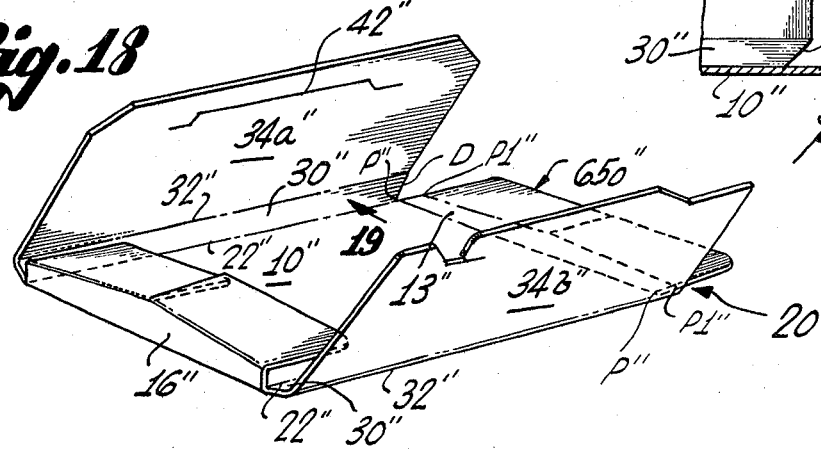
FIG. 18 is a perspective view showing the package of FIG. 17 in course of folding.
Figure 19:
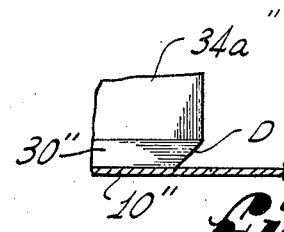
FIG. 19 is a detail view taken as indicated by the direction of the arrow 19 in FIG. 18.
Figure 20:
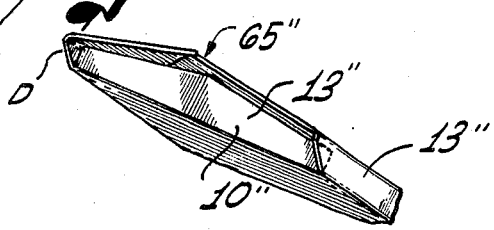
FIG. 20 is a view looking towards the closed end, remote from the viewer in FIG. 18.

The embodiment of FIGS. 18 to 20 is used in substantially the manner of FIGS. 13-16. After initial use of the unfolded package, and with the specimen on the glass slide mounted on the panel 10", the parts to the right of the severance lines 48", and of the disconnect lines D, and along the top edge of the panel 13", are detached and discarded.

Finally, with a specimen deposited on the glass slide (not shown in FIGS. 17-20), the carton, with the tear-away portion removed, is folded and locked closed, as shown in FIGS. 18 and 20.

The disconnect lines D are subject to wide variation in form. Ideally, excepting for difficulty of manufacture of the package, they may be formed of two right angle cuts, as in FIG. 1. However, the forming machine then requires two blades at right angles. The embodiment of FIG. 12 shows a single curved cut. That of FIG. 13 is the same as FIG. 12. A modification successfully used employs a curved blade of still greater radius of curvature and FIG. 17 shows an acceptable diagonal cut line. Broadly, the cut or disconnect line D can be by any path from point P" to point Ps".

The invention is subject to other changes and modifications within its broad scope without departure from the spirit and scope of the invention.

What is claimed is:

1. A rectangular package useable in a first form for initial containment of longitudinally extended articles, and convertible to a second longitudinally contracted, multiply reinforced form for transportation, comprising:

two rectangular, initially substantially rectilinearly aligned side panels, each having opposite longitudinal side edges, the corresponding side edges of the two panels being substantially rectilinearly aligned, the two side panels having both proximate and remote end edges, and an end wall interposed between and joining said proximate end edges of the side panels at spaced transverse score lines across said panels forming hinge joints and defining also the base and top edges of said end wall, said end wall having opposite end edges interposed between said corresponding longitudinal side edges of said side panels, another end wall attached at a base edge thereof to the remote end edge of one of said side panels, and a score line along said remote end edge of said one side panel enabling hinging of said end wall on said remote end edge of said one side panel, end flap means joined to the opposite edge of said last-mentioned end wall and separated therefrom by a score line forming a hinge;

longitudinal edge walls joined to the longitudinal edges of the side panels, and separated therefrom by score lines to enable bending therealong, side closure flaps joined to said longitudinal edge walls, and separated therefrom by score lines to enable bending therealong, said end edges of the end wall interposed between said side panels having disconnecting slits for at least the major portion of said edge walls between said top and base edges of said interposed end wall, said slits beginning substantially at the extremities of said base edge of said end wall, and the side closure flaps along each edge wall being separable into two independent flaps along tear lines of intermittent slits extending transversely of the package across said side closure flaps and said edge walls substantially toward and at least into general proximity with the upper corners of said interposed end wall, said lines of intermittent slits connecting end to end with the extremities of said disconnecting slits.

2. The subject matter of claim 1, wherein said slits follow generally along the end edges of the interposed end wall from the extremities of the base edge of said wall, and thence curve to confront, end to end, the inner ends of said tear lines of transversely extending intermittent slits.

3. The package of claim 1, including an end wall hinged to the remaining end of the other side wall, and flap means hinged to last last-mentioned end wall.

4. The package of claim 1, including an end wall hinged to the remaining end of the other side wall, and an implement holder hinged to said last-mentioned end wall.

5. The package of claim 1, wherein said lines of intermittent cuts comprise perforations across said side flaps and cuts across said edge walls.

6. The package of claim 1, wherein said end walls are elevated between the end edges thereof.

7. The package of claim 6, wherein said end walls have top edges in the general form of a saddle roof.

8. The package of claim 7, wherein said end walls have top edges comprised of two portions inclined upwardly in opposite directions from said upper end corners, and two end flaps hinged to said end wall along said two upwardly and oppositely inclined edge portions.

9. The package of claim 8, wherein said end flaps are separated by a V-notch.

10. The subject matter of claim 9, wherein said V-notch has a rounded bottom at the apex of said two oppositely inclined edge portions of said end walls.

11. The subject matter of claim 9, including also a rectangular glass slide affixed to the one of said side panels which has said end wall with said two end flaps hinged thereto, said glass slide being positioned generally longitudinally and centrally of said one side panel, with one end thereof alongside the end edge of said side panel to which is hinged the end wall with the two end flaps, said two end flaps having end corners engageable with said side panel outside the edges of said glass slide when the corresponding end wall is bent at right angles to the corresponding side panel and the end flaps are bent over on their hinge lines.

12. The subject matter of claim 1, including a transparent glass slide adhesively detachably affixed to the inner surface of said one of said side panels, and indicia printed on said inner side panel surface specially associated with respective separated areas of said glass slide on which different smear deposits may be made.

13. A generally rectangular multiply reinforced package for transportation of fragile articles, including:

two rectangular, initially substantially rectilinearly aligned side panels, each having opposite longitudinal side edges, the corresponding side edges of the two panels being substantially rectilinearly aligned, the two side panels having both proximate and remote end edges, and an end wall interposed between and joining said proximate end edges of the side panels at spaced transverse score lines across said panels forming hinge joints and defining also the base and top edges of said end wall, said end wall having opposite end edges interposed between said corresponding longitudinal side edges of said side panels, another end wall attached at a base edge thereof to the remote end edge of one of said side panels, and a score line along said remote end edge of said one side panel enabling hinging of said end wall on said remote end edge of said one side panel, end flap means joined to the opposite edge of said last-mentioned end wall and separated therefrom by a score line forming a hinge, longitudinal edge walls joined to the longitudinal edges of the side panels, and separated therefrom by score lines to enable bending therealong, side closure flaps joined to said longitudinal edge walls, and separated therefrom by score lines to enable bending therealong, said end edges of the end wall interposed between said side panels having disconnecting slits for a portion of said edge walls between said top and base edges of said interposed end wall, said slits beginning substantially at the extremities of said base edge of said end wall, and the side closure flaps along each edge wall being separated into two independent flaps along lines of separation extending transversely of the package across said side closure flaps and said edge walls substantially toward and at least into proximity with the upper corners of said interposed end wall, said lines of separation connecting end to end with the extremities of said disconnecting slits.

* * * * *